(12) United States Patent
Matthews et al.

(10) Patent No.: US 9,889,045 B2
(45) Date of Patent: *Feb. 13, 2018

(54) USER-FRIENDLY WELDING HELMET ASSEMBLY

(71) Applicant: Lincoln Global, Inc., City of Industry, CA (US)

(72) Inventors: William T. Matthews, Chesterland, OH (US); James Alan Harris, Painesville, OH (US); Joseph Daniel Lynch, III, Streetsboro, OH (US); Dino Anthony Mariano, Bridgeville, PA (US); Eric R. Colburn, Wexford, PA (US); Gregoire Aby-Eva, Pittsburgh, PA (US)

(73) Assignee: LINCOLN GLOBAL, INC., City of Industry, CA (US)

( * ) Notice: Subject to any disclaimer, the term of this patent is extended or adjusted under 35 U.S.C. 154(b) by 402 days.

This patent is subject to a terminal disclaimer.

(21) Appl. No.: 14/630,908

(22) Filed: Feb. 25, 2015

(65) Prior Publication Data
US 2015/0164694 A1 Jun. 18, 2015

Related U.S. Application Data

(63) Continuation of application No. 11/466,467, filed on Aug. 23, 2006, now Pat. No. 8,990,963.

(51) Int. Cl.
*A61F 9/06* (2006.01)
*A61F 9/02* (2006.01)
*F16P 1/06* (2006.01)

(52) U.S. Cl.
CPC .............. *A61F 9/06* (2013.01); *A61F 9/022* (2013.01); *A61F 9/061* (2013.01); *F16P 1/06* (2013.01)

(58) Field of Classification Search
CPC .............. A61F 9/061; A61F 9/022; F16P 1/06
See application file for complete search history.

(56) References Cited

U.S. PATENT DOCUMENTS

| | | | |
|---|---|---|---|
| 2,187,542 A | 1/1940 | Hagen | |
| 2,187,932 A | 1/1940 | Cornell | |
| 2,411,224 A * | 11/1946 | O'Reilly | A61F 9/061 2/8.3 |
| 3,041,622 A | 7/1962 | Gurtowski | |
| 3,075,201 A | 1/1963 | Lindblom | |
| 3,079,609 A | 3/1963 | Hoffmaster | |
| 3,090,046 A | 5/1963 | Bowers, Sr. | |
| 3,156,922 A | 11/1964 | Anderson | |

(Continued)

FOREIGN PATENT DOCUMENTS

CN 2262907 Y 9/1997
WO 2008/024555 A2 3/2015

*Primary Examiner* — Tejash Patel (57) ABSTRACT

User-friendly welding helmet assembly configurations to be worn on the head of a weldor are disclosed. The welding helmet assembly configurations include various advanced features including a spatter shield that is easily replaceable from an external front portion of a shell of the helmet assembly configuration, and an adjustable ratchet headgear within the shell having a repositionable lever adapted to easily adjust a detent position of the ratchet headgear with respect to the shell. Other user-friendly features are also provided, in accordance with various embodiments of the present invention.

31 Claims, 8 Drawing Sheets

(56) References Cited

U.S. PATENT DOCUMENTS

| | | |
|---|---|---|
| 3,444,560 A | 5/1969 | Northup, Jr. |
| 3,866,244 A | 2/1975 | Ruck |
| 3,984,875 A | 10/1976 | Farquharson |
| 4,039,254 A | 8/1977 | Harsch |
| 4,039,803 A | 8/1977 | Harsch |
| RE29,684 E | 6/1978 | Gordon |
| 4,114,198 A | 9/1978 | Sands |
| D249,827 S | 10/1978 | Rieppel et al. |
| 4,117,554 A | 10/1978 | Palumbo |
| D250,856 S | 1/1979 | Siebert |
| 4,185,328 A | 1/1980 | Graveno |
| 4,237,557 A | 12/1980 | Gordon |
| 4,241,286 A | 12/1980 | Gordon |
| D267,207 S | 12/1982 | Hilton |
| 4,373,212 A | 2/1983 | West |
| 4,422,185 A | 12/1983 | Cook |
| 4,464,800 A | 8/1984 | Edwards |
| 4,523,808 A | 6/1985 | Miller et al. |
| 4,525,876 A | 7/1985 | Bailey |
| 4,556,991 A | 12/1985 | Margaronis et al. |
| 4,649,571 A | 3/1987 | Falkiner |
| 4,774,723 A | 10/1988 | Ruck |
| D298,421 S | 11/1988 | Tyroff |
| 4,853,973 A | 8/1989 | Boochard |
| 4,863,244 A | 9/1989 | Fuerthbauer et al. |
| D308,586 S | 6/1990 | Van Wyk |
| 4,937,879 A | 7/1990 | Hall et al. |
| 4,942,628 A | 7/1990 | Freund |
| D310,276 S | 8/1990 | Fuerthbauer et al. |
| D310,432 S | 9/1990 | Boochard |
| D316,164 S | 4/1991 | Furthbauer et al. |
| 5,029,342 A | 7/1991 | Stein et al. |
| 5,031,237 A | 7/1991 | Honrud |
| 5,074,647 A | 12/1991 | Fergason et al. |
| 5,140,707 A | 8/1992 | Johnson |
| 5,191,468 A | 3/1993 | Mases |
| 5,224,219 A | 7/1993 | Edwards et al. |
| 5,333,329 A | 8/1994 | Hong |
| 5,357,654 A | 10/1994 | Hsing-Chi |
| 5,377,032 A | 12/1994 | Fergason et al. |
| D365,366 S | 12/1995 | Cerrato |
| 5,515,186 A | 5/1996 | Fergason et al. |
| 5,519,522 A | 5/1996 | Fergason et al. |
| 5,533,206 A | 7/1996 | Petrie et al. |
| 5,561,855 A | 10/1996 | McFall |
| 5,571,217 A | 11/1996 | Del Bon et al. |
| 5,619,754 A | 4/1997 | Thurwanger et al. |
| 5,669,070 A | 9/1997 | Bennett et al. |
| 5,749,096 A | 5/1998 | Fergason et al. |
| 5,793,449 A | 8/1998 | Lagerwall |
| 5,806,101 A | 9/1998 | Thurwanger et al. |
| 5,813,049 A | 9/1998 | Xu |
| 5,857,215 A | 1/1999 | Fergason et al. |
| 5,896,579 A | 4/1999 | Johnson et al. |
| 5,950,245 A | 9/1999 | Binduga |
| 6,035,451 A * | 3/2000 | Burns ............ A42B 3/10 2/424 |
| 6,049,911 A | 4/2000 | Bromberg |
| 6,070,264 A | 6/2000 | Hamilton et al. |
| D431,328 S | 9/2000 | Tanner |
| 6,151,711 A | 11/2000 | Edwards |
| 6,178,552 B1 | 1/2001 | Robinson |
| 6,185,739 B1 | 2/2001 | Verkic et al. |
| D444,919 S | 7/2001 | Kramer et al. |
| 6,260,197 B1 | 7/2001 | Hoogewind |
| 6,270,223 B1 | 8/2001 | Del Bon et al. |
| 6,317,643 B1 | 11/2001 | Dmochowski |
| 6,341,381 B1 | 1/2002 | Rink, Jr. |
| 6,370,695 B2 | 4/2002 | Paris et al. |
| 6,393,617 B1 | 5/2002 | Paris et al. |
| 6,401,244 B1 | 6/2002 | Kramer et al. |
| 6,557,174 B2 | 5/2003 | Martin et al. |
| 6,815,652 B1 | 11/2004 | Hamilton |
| 6,855,922 B2 | 2/2005 | Hamilton |
| 6,891,681 B2 | 5/2005 | Schindele |
| 6,973,672 B2 | 12/2005 | Huh |
| 8,990,963 B2 | 3/2015 | Matthews et al. |
| 2001/0037519 A1 | 11/2001 | Paris et al. |
| 2001/0039671 A1 | 11/2001 | Robinson et al. |
| 2002/0024739 A1 | 2/2002 | Martin et al. |
| 2003/0106138 A1 | 6/2003 | Guay |
| 2003/0110548 A1 | 6/2003 | Robinson et al. |
| 2004/0078859 A1 | 4/2004 | Inget et al. |
| 2004/0083539 A1 | 5/2004 | Schindele |
| 2004/0195489 A1 | 10/2004 | Hamilton |
| 2004/0251097 A1 | 10/2004 | Huh |
| 2005/0017152 A1 | 1/2005 | Fergason |
| 2006/0010551 A1 | 1/2006 | Bishop et al. |

* cited by examiner

USER-FRIENDLY WELDING HELMET ASSEMBLY

This U.S. patent application claims priority to and is a continuation patent application of pending U.S. patent application Ser. No. 11/466,467 filed on Aug. 23, 2006, which is incorporated by reference herein in its entirety.

TECHNICAL FIELD

Certain embodiments of the present invention relate to welding helmets. More particularly, certain embodiments of the present invention relate to re-configurable welding helmet assemblies with user-friendly features.

BACKGROUND OF THE INVENTION

A welding helmet is typically used during a welding process to help protect the weldor from various dangers such as sparks, heat, and flashes of light (e.g., visible light, ultraviolet light, and infrared light). A typical welding helmet covers the front and/or sides of the head of the weldor and includes a relatively transparent front portion to see through. The intense heat and brightness associated with welding can cause eye damage including, possibly, blindness. Therefore, a filter lens is typically used to filter out harmful light and heat.

A spatter shield on the front of the welding helmet helps protect the weldor as well as the filter from flying sparks and other debris that may fly towards the helmet during a welding operation. The spatter shield frequently becomes scratched or damaged and must be replaced so as not to hinder the view of the weldor. Gaining access to the spatter shield is often difficult and time-consuming, requiring other elements (such as a filter) to be removed in order to remove the spatter shield. Many times the spatter shield has to be removed from the interior of the helmet shell, which can be difficult, especially if the user (i.e., weldor) has large hands and fingers.

Being able to adjust the helmet to tilt at a proper angle with respect to the weldor's head and eyes is often difficult to accomplish. The weldor may have to remove the helmet, adjust it, and try it on again to see if the adjustment is correct. The weldor may have to repeat this process several times before the angle of the helmet is adjusted to a desirable position. Also, adjusting controls on an automatic darkening filter (ADF) shade cartridge, which is being used as the filter, may be difficult and time consuming, requiring various elements of the helmet to be dis-assembled to get at the controls, and then re-assembled once the controls are adjusted. This process may have to be repeated several times as well, until the weldor gets the adjustments just right.

For certain applications, a weldor may want to use one type of helmet configuration and, for certain other applications, a weldor may want to use a slightly different type of helmet configuration. Such circumstances typically require the weldor to have two or more separate helmets that he can switch between. Each helmet may require a unique set of elements such as filters, lenses, cover plates, and shields. Also, each helmet has to be adjusted to a fit of the weldor and to other preferences of the weldor for a particular application.

In general, many welding helmets today are not very user-friendly and require a user to spend a significant amount of time making adjustments and replacing various elements.

Further limitations and disadvantages of conventional, traditional, and proposed approaches will become apparent to one of skill in the art, through comparison of such systems and methods with the present invention as set forth in the remainder of the present application with reference to the drawings.

BRIEF SUMMARY OF THE INVENTION

A first embodiment of the present invention comprises a re-configurable welding helmet assembly to be worn on the head of a weldor. The re-configurable welding helmet assembly includes a common shell having a first open window at a front portion of the common shell. The common shell is adaptable to at least two different welding helmet configurations. The welding helmet assembly further includes an interior lens and an interior retaining mechanism to retain the interior lens over the first open window. The welding helmet assembly further includes a front bezel having a second open window and being adapted to easily attach to and detach from an exterior front portion of the common shell such that the second open window aligns substantially with the first open window when the front bezel is attached to the common shell. The welding helmet assembly also includes a spatter shield positioned externally to the common shell proximate the front portion of the common shell by, at least in part, the front bezel such that the spatter shield is easily accessible from the external front portion of the common shell for replacement.

A second embodiment of the present invention comprises a welding helmet assembly to be worn on the head of a weldor. The welding helmet assembly includes a shell having a first open window at a front portion of the shell. The welding helmet assembly further includes a bezel adapter having a second open window and being adapted to easily attach to and detach from an exterior front portion of the shell such that the second open window aligns substantially with the first open window when the bezel adapter is attached to the shell. The welding helmet assembly also includes a filter lens adapted to fit securely between the first open window of the shell and the second open window of the bezel adapter when the bezel adapter is attached to the shell. The welding helmet assembly further includes a bezel having a third open window and being adapted to easily attach to and detach from the exterior front portion of the shell over the bezel adapter such that the third open window aligns substantially with the second open window and the first open window when the bezel adapter and the bezel are attached to the shell. The welding helmet assembly also includes a spatter shield adapted to fit securely between the second open window of the bezel adapter and the third open window of the bezel when the bezel adapter and the bezel are attached to the shell such that the spatter shield is easily accessible from the exterior front portion of the shell for replacement. The welding helmet assembly further includes a clear cover plate adapted to slide upward into an interior front portion of the shell to cover the first open window behind the filter lens.

Another embodiment of the present invention comprises a welding helmet assembly to be worn on the head of a weldor. The welding helmet assembly includes a means for retaining at least one lens at a front portion of a shell of the welding helmet assembly to cover an open window of the shell. The welding helmet assembly further includes a means for retaining a spatter shield at an external front portion of the shell such that the spatter shield is in substantial alignment with the open window. The welding helmet assembly also includes a means for easily accessing the spatter shield for replacement at the external front portion of the shell without having to remove the at least one lens from the shell. The welding helmet assembly further includes a means to adjust a detent position, with respect to the shell, of an adjustable headgear mounted within the shell. The detent position determines a centering of the shell with respect to the headgear by defining how far upward and how far downward the shell can tilt with respect to a reference plane through the headgear.

These and other advantages and novel features of the present invention, as well as details of illustrated embodiments thereof, will be more fully understood from the following description and drawings.

DETAILED DESCRIPTION OF THE INVENTION

Figure 1:
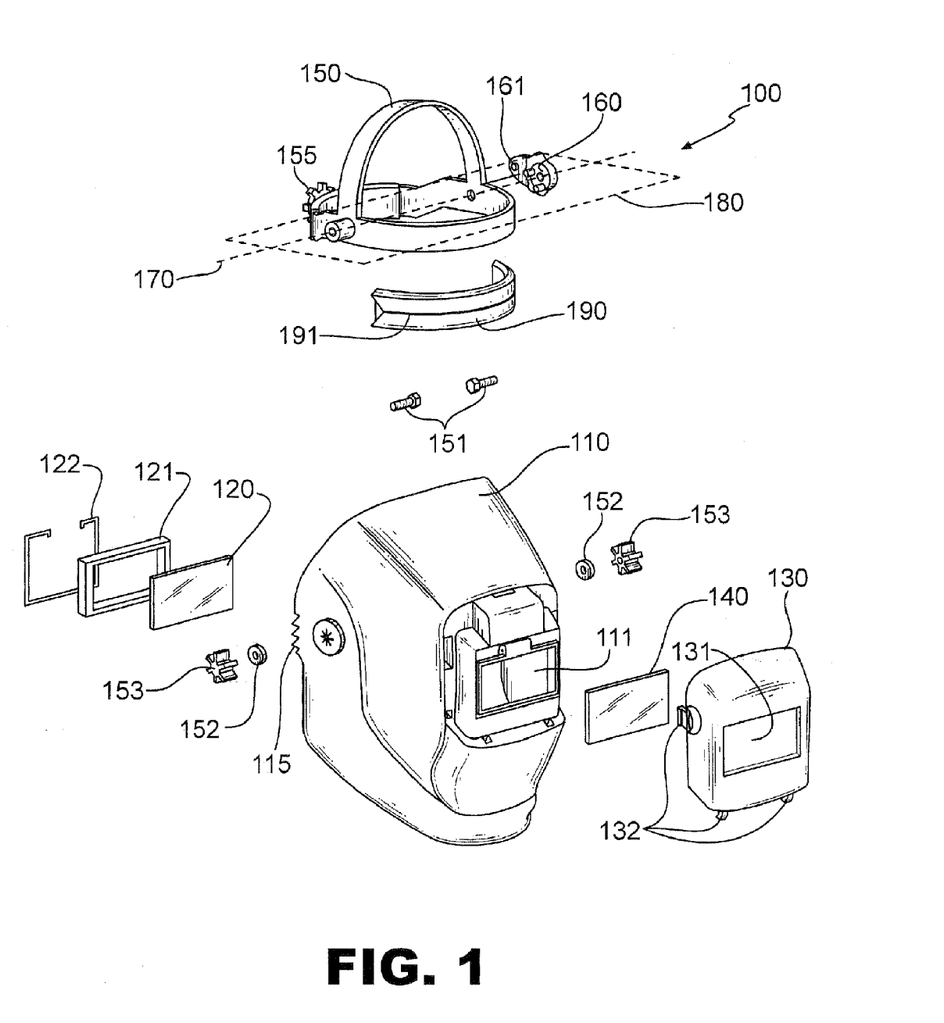
FIG. 1 is an exemplary illustration of an exploded view of a first embodiment of a welding helmet assembly corresponding to a first configuration using a common shell, in accordance with various aspects of the present invention.

FIG. 1 is an exemplary illustration of an exploded view of a first embodiment of a welding helmet assembly 100 corresponding to a first configuration using a common shell 110, in accordance with various aspects of the present invention. The common shell 110 may be used in several different welding helmet configurations, as will be described herein. A front portion of the shell 110 includes an open window 111 which defines a maximum viewing window for a weldor using the helmet assembly 100. The first open window 111 has dimensions of 2 inches by 4 inches, in accordance with an embodiment of the present invention. Other window dimensions are possible as well such as, for example, a 90 mm×110 mm window size which is standard in Europe.

An interior lens comprising a fixed filter lens 120 is adapted to cover the open window 111 at an interior front portion of the shell 110. The fixed filter lens 120 may be any type of fixed filter lens known in the art serving the purpose of protecting a weldor's eyes from the glare of a welding arc while using the welding helmet configuration 100 during a welding process. An interior retaining frame 121 is adapted to help retain the fixed filter lens at the interior front portion of the shell 110 over the open window 111. A de-latchable interior retaining clip 122 is adapted to secure the fixed filter lens 120 and the interior retaining frame 121 in place at the interior front portion of the common shell 110 over the first open window 111. The interior retaining frame 121 and the interior retaining clip 122 constitute an interior retaining mechanism, in accordance with an embodiment of the present invention. Other interior retaining mechanisms are possible as well, in accordance with various alternative embodiments of the present invention.

A front bezel 130 having a second open window 131 is adapted to easily attach to and detach from an exterior front portion of the common shell 110. The second open window 131 aligns substantially with the first open window 111 when the front bezel 130 is attached to the common shell 110 at the exterior front portion of the common shell 110. The front bezel 130 includes plastic tabs 132 around the front bezel 130 that snap into openings in the common shell 110.

In accordance with an embodiment of the present invention, a spatter shield 140 is held in position between the first open window 111 of the common shell 110 and the second open window 131 of the front bezel 130 when the front bezel 130 is attached to the common shell 110. The spatter shield 140 helps protect the eyes of the weldor and the lens (or ADF) and is easily accessible from the external front portion of the common shell 110 for replacement by detaching the front bezel 130 from the common shell 110. When the spatter shield becomes scratched or spattered during a welding process, replacement of the spatter shield is accomplished without having to remove any filter lens (e.g., fixed filter lens 120) from the welding helmet assembly 100.

In order to properly fit a head of a weldor to the welding helmet assembly 100, an adjustable ratchet headgear 150 is mounted within an interior of the common shell 110 via headgear mounting hardware 151, 152 and 153. The ratchet headgear 150 allows the common shell 110 to tilt upward and downward with respect to the ratchet headgear 150. A repositionable lever 160 attaches to one side of the ratchet headgear 150 and is adapted to adjust a detent position of the ratchet headgear 150 with respect to the common shell 110. The detent position determines a centering of the common shell 110 with respect to the ratchet headgear 150 by defining how far up and how far down the common shell may tilt about an imaginary axis 170 with respect to an imaginary reference plane (e.g., 180) through the ratchet headgear 150. The ratchet headgear 150 includes a ratchet knob 155 at the back of the headgear 150 for adjusting a fit of the headgear 150 to a weldor's head. The knob 155 is simply pushed inward and rotated left or right to adjust the fit.

The repositionable lever 160 may be locked into any one of a plurality of detent positions via a tab 161 on the lever 160 that fits into one of a plurality of visible ridges or notches 115 on a side edge of the common shell 110 (shown on a side of the shell 110 opposite that of the lever 160 in FIG. 1 simply for illustrative purposes). Each visible ridge of the plurality of visible ridges 115 corresponds to and identifies a different locked detent position of the plurality of possible detent positions.

In accordance with an embodiment of the present invention, the headgear mounting hardware includes a pair of mounting bolts 151, a pair of mounting washers 152, and a pair of mounting nuts 153, one of each pair mounted on opposite sides of the shell 110. The bolts 151 pass through holes in the common shell 100 to connect the headgear 150 to the shell 110 via the nuts 153 and washers 152. The mounting washers 152 are adapted to provide frictional force between the common shell 110 and the ratchet headgear 150. In accordance with an embodiment of the present invention, there are raised patterns adjacent where the mounting washers sit that help provide the frictional force as the washers fit against the raised patterns. The amount of frictional force may be adjusted by the pair of mounting nuts 153 to set a speed of tilt of the common shell 110 with respect to the headgear 150.

The ratchet headgear 150 is totally adjustable for fit, speed of tilt, and detent tilt position while the weldor is wearing the welding helmet assembly 100. As a result, the weldor can immediately determine if the adjustments are satisfactory without having to remove the helmet.

As an option, a sweatband 190 may be provided which removably attaches to a front portion of the ratchet headgear 150 such that the sweatband 190 touches and spans a forehead of a weldor when the welding helmet assembly 100 is properly fitted to and worn by a weldor. In accordance with an embodiment of the present invention, the sweatband 190 includes a slot 191 spanning a front portion of the sweatband 190 which may be opened and then closed to attach the sweatband 190 to the headgear 150.

Figure 2:
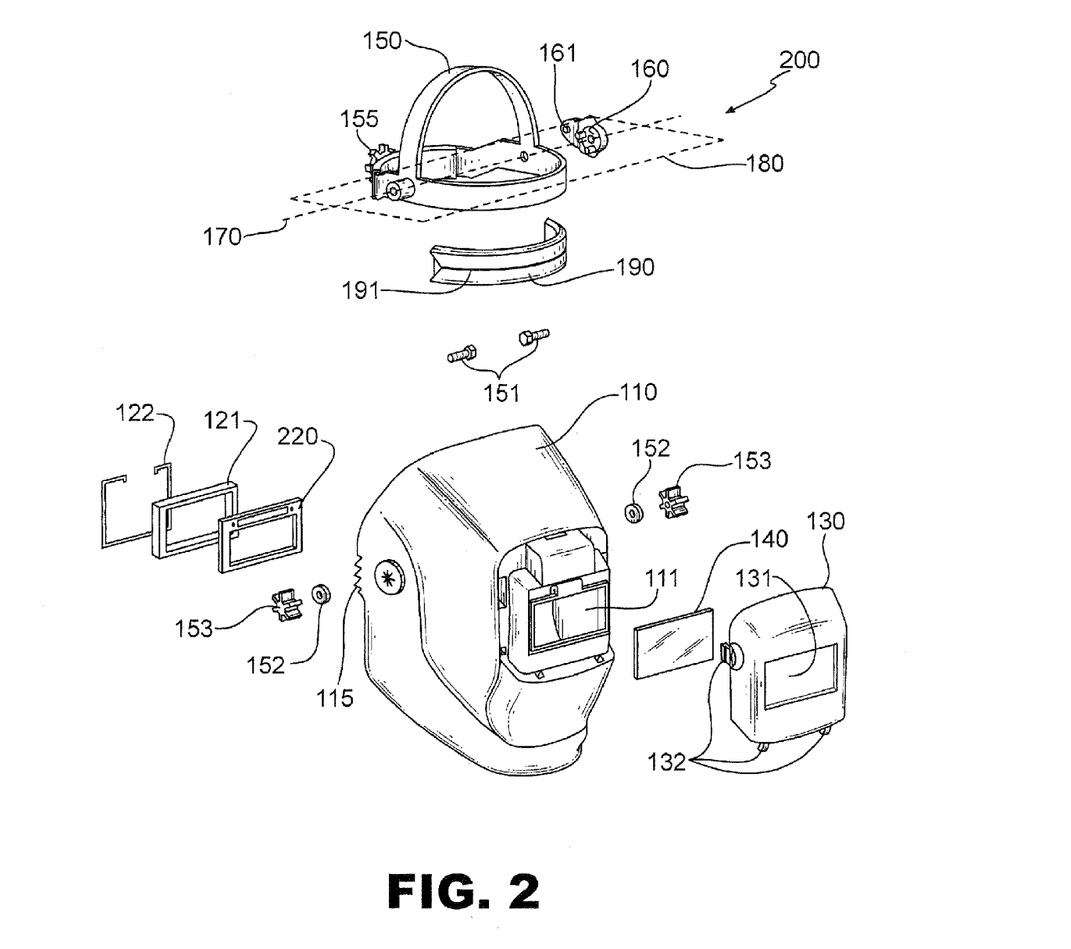
FIG. 2 is an exemplary illustration of an exploded view of a second embodiment of a welding helmet assembly corresponding to a second configuration using the common shell of FIG. 1, in accordance with various aspects of the present invention.

FIG. 2 is an exemplary illustration of an exploded view of a second embodiment of a welding helmet assembly 200 corresponding to a second configuration using the common shell 110 of FIG. 1, in accordance with various aspects of the present invention. The welding helmet assembly 200 is the same as the welding helmet assembly 100 of FIG. 1 except that, instead of a fixed filter lens 120, the welding helmet assembly 200 includes an auto darkening filter (ADF) shade cartridge 220. Such an ADF shade cartridge 220 functions to protect the eyes of a weldor, in a more sophisticated manner than a simple fixed filter lens, by automatically sensing incident light and enabling at least one dark state of the filter when the intensity of the incident light is high enough. Otherwise, the state of the filter is relatively clear. The ADF shade cartridge 220 may have several intermediate darkening states where the darkening state that is enabled depends on the sensed intensity of the incident light. The ADF shade cartridge 220 is held in place over the window 111 at a front interior portion of the common shell 110 by the retaining frame 121 and retaining clip 122, similar to that previously described for the fixed filter lens 120.

Figure 3:
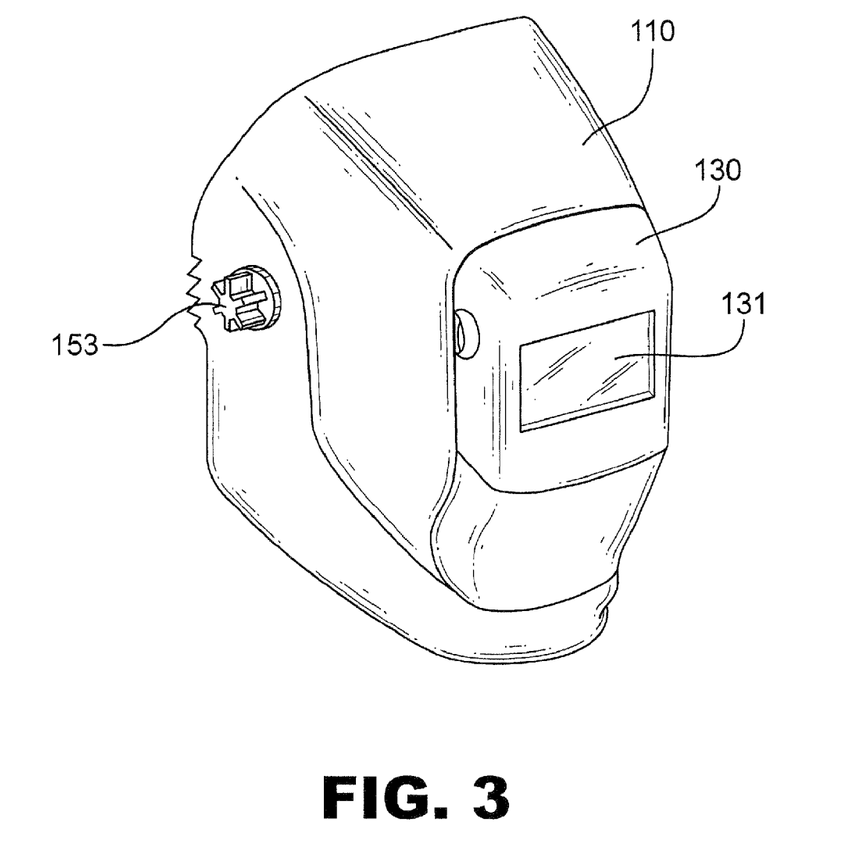
FIG. 3 is an exemplary illustration of an external perspective view of the fully assembled welding helmet assembly embodiments of FIG. 1 and FIG. 2, in accordance with various aspects of the present invention.

FIG. 3 is an exemplary illustration of an external perspective view of the fully assembled welding helmet assembly embodiments 100 and 200 of FIG. 1 and FIG. 2, in accordance with various aspects of the present invention. In the perspective view, the common shell 110, the front bezel 130, the window 131, and the mounting nut 152 are clearly seen.

Figure 4:
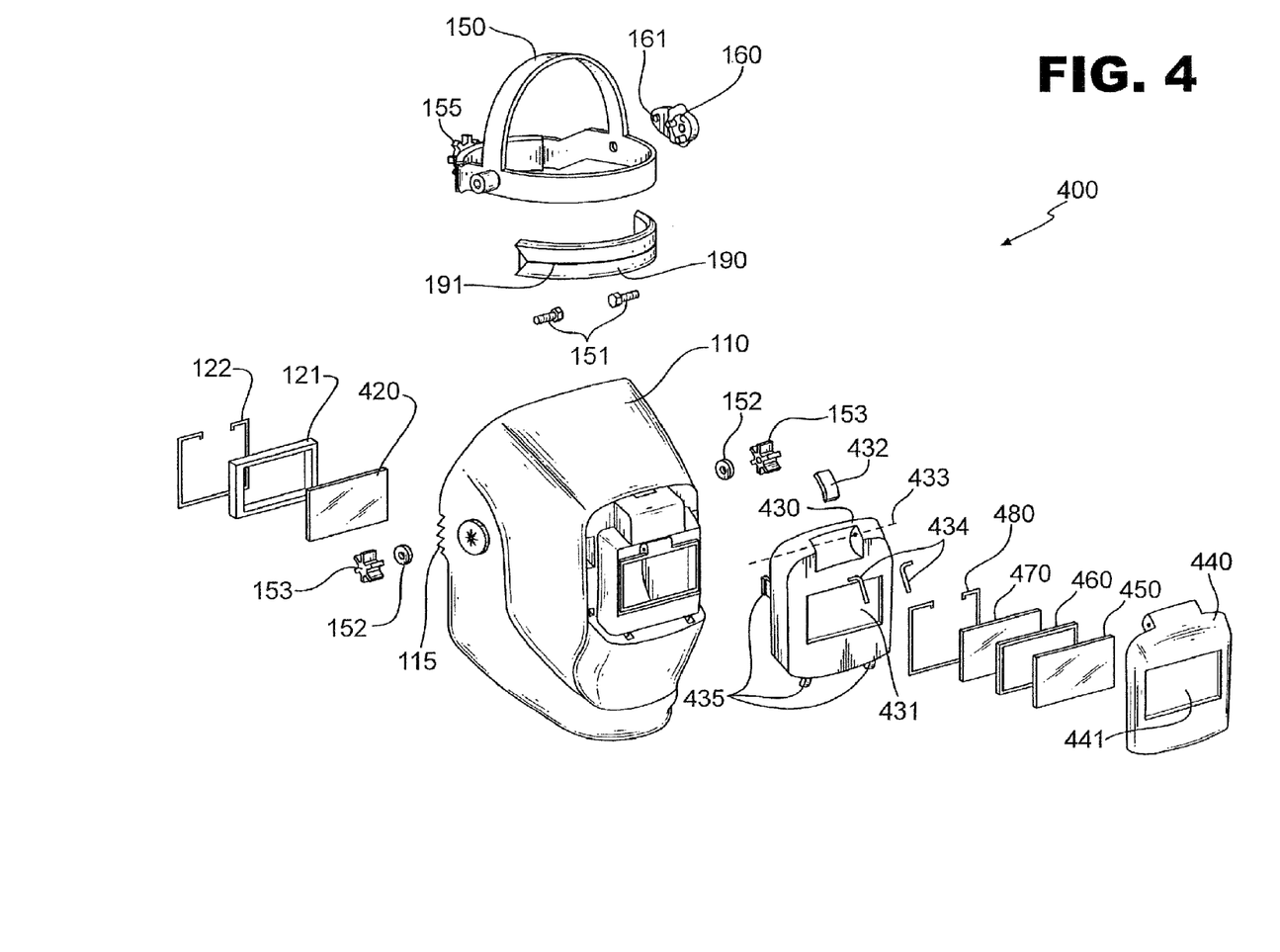
FIG. 4 is an exemplary illustration of an exploded view of a third embodiment of a welding helmet assembly corresponding to a third configuration using the common shell of FIG. 1, in accordance with various aspects of the present invention.

FIG. 4 is an exemplary illustration of an exploded view of a third embodiment of a welding helmet assembly 400 corresponding to a third configuration using the common shell 110 of FIG. 1, in accordance with various aspects of the present invention. As described previously, a front portion of the shell 110 includes an open window 111 which defines a maximum viewing window for a weldor using the helmet assembly 400.

An interior lens comprising a clear plastic lens 420 is adapted to cover the open window 111 at an interior front portion of the shell 110. An interior retaining frame 121 is adapted to help retain the clear plastic lens 420 at the interior front portion of the shell 110 over the open window 111. A de-latchable interior retaining clip 122 is adapted to secure the clear plastic lens 420 and the interior retaining frame 121 in place at the interior front portion of the common shell 110 over the first open window 111. The interior retaining frame 121 and the interior retaining clip 122 constitute an interior retaining mechanism, in accordance with an embodiment of the present invention. Other interior retaining mechanisms are possible as well, in accordance with various alternative embodiments of the present invention. In the configuration of FIG. 4, any filter lens is external to the common shell 110 as will be described herein.

A front bezel 430 having a second open window 431 is adapted to easily attach to and detach from an exterior front portion of the common shell 110. The second open window 431 aligns substantially with the first open window 111 when the front bezel 430 is attached to the common shell 110 at the exterior front portion of the common shell 110. In accordance with an embodiment of the present invention, the front bezel 430 includes tabs 435 that snap into openings in the common shell 110.

The front bezel 430 snaps onto the common shell 110 in the same manner that the front bezel 130 of FIG. 1 snaps onto the common shell 110. However, the front bezel 430 is different from the front bezel 130 of FIG. 1 in that the front bezel 430 is adapted to accept a lift mechanism such as, for example, a pivot pin 434 and a lift spring 432, which enables a flip bezel 440 to connect to the front bezel 430. The flip bezel 440 includes a third open window 441. The flip bezel 440 is adapted to attach to the front bezel 430 via the pivot pin 434 and lift spring 432 at a top portion of the flip bezel 440 such that the flip bezel 440 is capable of being flipped upward and downward, with respect to the front bezel 430, about an imaginary pivot axis 433 through a top/front portion of the front bezel 430. Other flip mechanisms may be employed which perform the same function as the pivot pin 434 and lift spring 432, in accordance with various alternative embodiments of the present invention.

When the flip bezel 440 is flipped downward, the third open window 441 of the flip bezel 440 aligns substantially with the second open window 431 of the front bezel 430 and the first open window 111 of the common shell 110. The lift spring 432 provides tension between the front bezel 430 and the flip bezel 440 to keep the flip bezel 440 in the up or down position, until moved by a user of the helmet assembly 400.

A spatter shield 450 is adapted to cover the open window 441 at an inside portion of the flip bezel 440. A forward filter lens 460 is positioned directly behind the spatter shield 450 away from the third open window 441. The forward filter lens 460 may comprise a fixed filter lens or an ADF shading cartridge, in accordance with various embodiments of the present invention. A clear cover plate 470 is positioned directly behind the forward filter lens 460 away from the third open window. A de-latchable forward retaining clip 480 is adapted to secure the clear cover plate 470, the forward filter lens 460, and the spatter shield 450 in a sandwiched configuration at an inside portion of the flip bezel 440 to cover the third open window 441. The spatter shield 450 protects the forward filter lens 460 from the front, and the clear cover plate 470 protects the forward filter lens 460 from the rear. The spatter shield 450 may be easily accessed for replacement by flipping upward the flip bezel 440 and de-latching the forward retaining clip 480 to remove the sandwiched configuration of the clear cover plate 470, the forward filter lens 460, and the spatter shield 450.

Certain other elements of the welding helmet assembly 400 are the same as, and have the same function as, those corresponding elements of the welding helmet assembly 100 of FIG. 1 and FIG. 2, including the ratchet headgear 150, the repositionable lever 160, the headgear mounting hardware 151-153, and the sweatband 190 as previously described herein.

Figure 5:
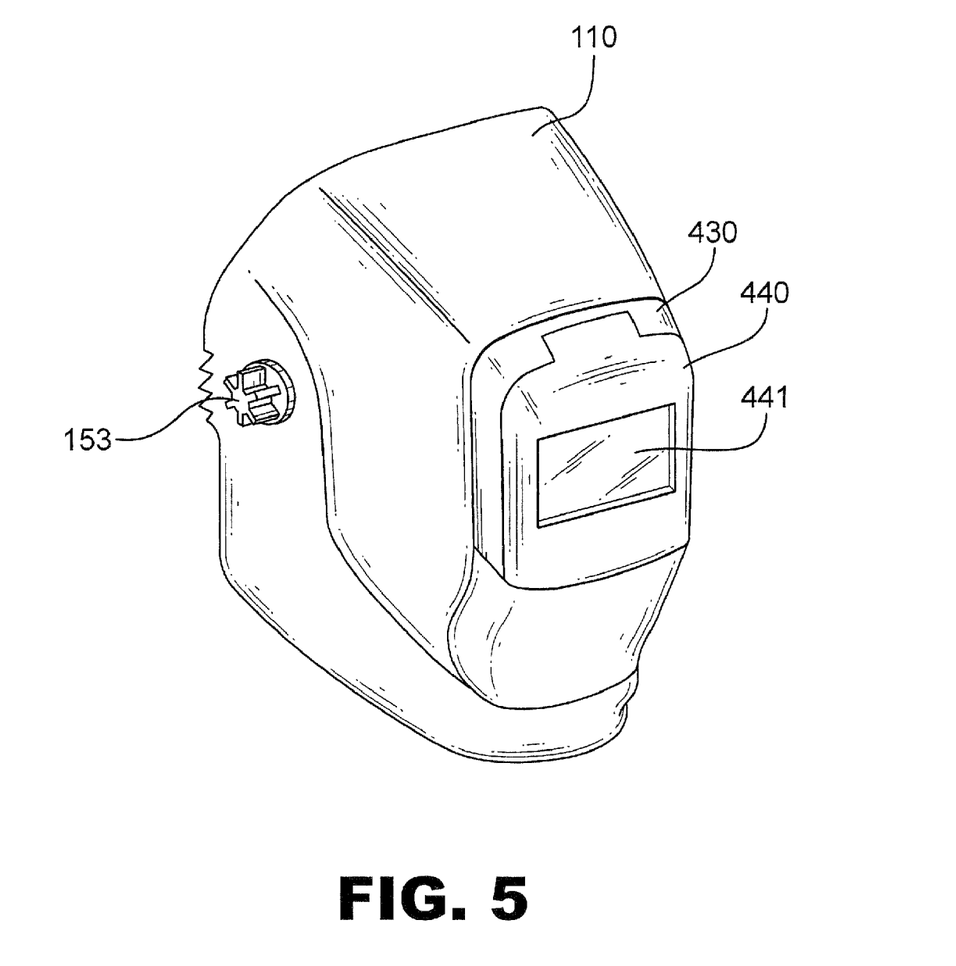
FIG. 5 is an exemplary illustration of an external perspective view of the fully assembled welding helmet assembly embodiment of FIG. 4, in accordance with various aspects of the present invention.

FIG. 5 is an exemplary illustration of an external perspective view of the fully assembled welding helmet assembly embodiment 400 of FIG. 4, in accordance with various aspects of the present invention. In the perspective view, the common shell 110, the front bezel 430, the flip bezel 440, the window 441, and the mounting nut 153 are clearly seen.

The resultant configuration of FIGS. 4-5 allow a weldor to flip the bezel 440, having the filter lens 460 mounted to it, upward and downward as the weldor sees fit during a welding process. When the flip bezel 440 is flipped downward, the filter lens 460 is in place to protect the weldor's eyes. When the flip bezel 440 is flipped upward, the lens is removed from the weldor's view and the weldor can see clearly through the helmet assembly. In the configurations of FIGS. 1-3, the filter lens is instead mounted at an interior front portion of the common shell 110. However, in all of the configurations of FIGS. 1-5, the spatter shield is accessible for replacement, exterior to the common shell 110 at a front portion of the common shell 110.

Figure 6:
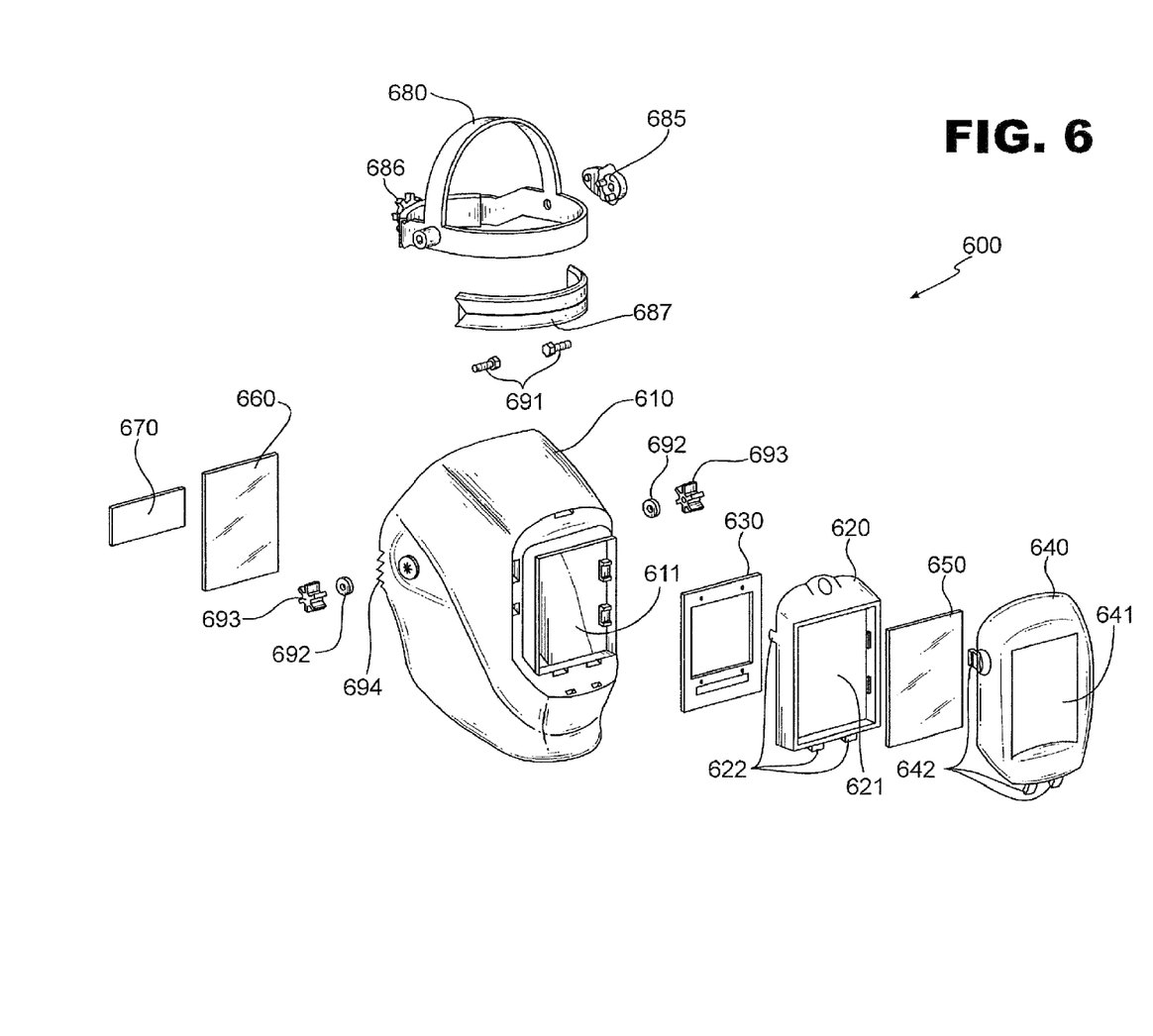
FIG. 6 is an exemplary illustration of an exploded view of a fourth embodiment of a welding helmet assembly using a different shell from that of the embodiments of FIGS. 1-5, in accordance with various aspects of the present invention.

FIG. 6 is an exemplary illustration of an exploded view of a fourth embodiment of a welding helmet assembly 600 using a different shell 610 from that of the embodiments of FIGS. 1-5, in accordance with various aspects of the present invention. The shell 610 of the welding helmet assembly 600 includes a first open window 611 at a front portion of the shell 610. The first open window 611 has dimensions of 4 inches by 5 inches, in accordance with an embodiment of the present invention. Other window dimensions are possible as well.

The welding helmet assembly 600 also includes a bezel adapter 620 having a second open window 621. The bezel adapter 620 is adapted to easily attach to and detach from an exterior front portion of the shell 610 such that the second open window 621 aligns substantially with the first open window 611 when the bezel adapter 620 is attached to the shell 610. The bezel adapter 620 includes plastic tabs 622 around the bezel adapter 620 that snap into openings in the shell 610, in accordance with an embodiment of the present invention.

The welding helmet assembly 600 further includes a filter lens 630 adapted to fit securely between the first open window 611 of the shell 610 and the second open window 621 of the bezel adapter 620 when the bezel adapter 620 is attached to the shell 610. The filter lens 630 may comprise a fixed filter lens or an ADF shading cartridge, in accordance with various embodiments of the present invention. In accordance with an embodiment of the present invention, spring fingers around the second window 621 of the bezel adapter 620 help to secure the filter lens 630 against tabs around the first open window 611 of the shell 610.

The welding helmet assembly 600 also includes a bezel 640 having a third open window 641 and being adapted to easily attach to and de-tach from the exterior front portion of the shell 610 over the bezel adapter 620. The third open window 641 aligns substantially with the second open window 621 and the first open window 611 when the bezel adapter 620 and the bezel 640 are attached to the shell 610. The bezel 640 includes plastic tabs 642 around the bezel 640 that snap into openings in the shell 610, in accordance with an embodiment of the present invention.

The welding helmet assembly 600 further includes a spatter shield 650 adapted to fit securely between the second open window 621 of the bezel adapter 620 and the third open window 641 of the bezel 640 when the bezel adapter 620 and the bezel 640 are attached to the shell 610. As a result, the spatter shield 650 is easily accessible from the exterior front portion of the shell 610 for replacement simply by de-taching the bezel 640 from the shell 610.

A clear cover plate 660 is adapted to slide upward into an interior front portion of the shell 610 to cover the first open window 611 behind the filter lens 630 to help protect the filter lens 630. Also, as an option, an adjustable cheater plate 670 is adapted to slide upward into the interior front portion of the shell 610 behind the clear cover plate 660. A position of the cheater plate 670 is adjustable, independent of the clear cover plate 660, to an eye level of a weldor using the welding helmet assembly 600. The cheater plate 670 allows a weldor to not have to use eye glasses while wearing the welding helmet assembly 600. In accordance with an embodiment of the present invention, the cheater plate 670 is a bi-focal corrective lens that serves to correct the less than perfect vision of the weldor.

In accordance with an embodiment of the present invention, the clear cover plate 660 is slidably held in position over the first window 611 by a plurality of tabs on the shell 610 surrounding the first window 611 at an interior portion of the shell 610. The clear cover plate 660 may be removed from the shell 610 by sliding the clear cover plate 660 downward past the tabs, whether or not the cheater plate 670 is installed in the shell 610. Also, the adjustable cheater plate 670 is slidably held in position by a plurality of tabs on the shell surrounding the first window. Means, other than tabs, may also be used to allow sliding and holding of the clear cover plate 660 and the cheater plate 670, in accordance with various alternative embodiments of the present invention.

The welding helmet assembly 600 also includes a ratchet headgear 680 with a repositionable lever 685, a ratchet knob 686, mounting hardware 691-693 and, optionally, a sweatband 687 functioning the same as the corresponding elements of FIG. 1, for example, as described previously herein.

Figure 7:
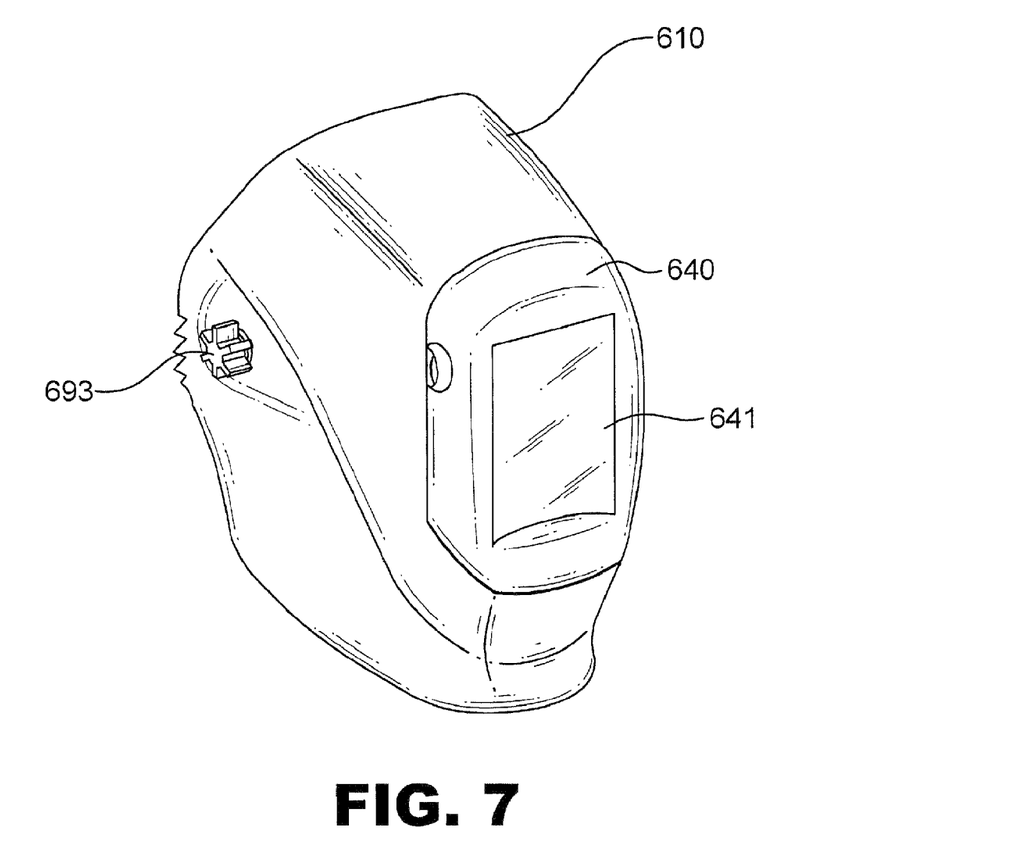
FIG. 7 is an exemplary illustration of a perspective view of the fully assembled welding helmet assembly of FIG. 6, in accordance with various aspects of the present invention.

FIG. 7 is an exemplary illustration of a perspective view of the fully assembled welding helmet assembly 600 of FIG. 6, in accordance with various aspects of the present invention. In the perspective view, the shell 610, the bezel 640, the window 641, and the mounting nut 693 are clearly seen. The bezel adapter 620 is covered and hidden by the bezel 640.

In accordance with an embodiment of the present invention, when the filter lens 630 is an ADF shade cartridge, the clear cover plate 660 may be slid further upward to expose a set of common controls on a lower portion of the shade cartridge 630, whether or not the adjustable cheater plate 670 is installed. As a result, a weldor can easily access the set of common controls of the ADF shade cartridge 630 to control the resultant operation of the ADF shade cartridge 630 without having to totally remove the clear cover plate 660.

Figure 8A:
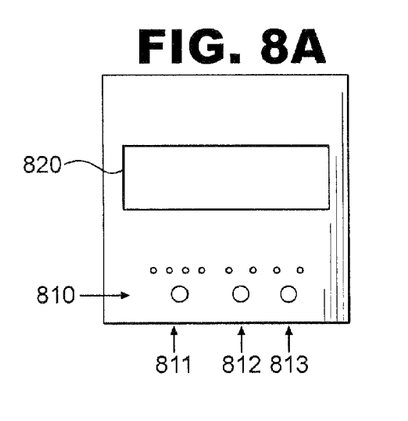
FIGS. 8A-8C illustrate three exemplary embodiments of auto darkening shade cartridges, having a common set of controls and different window sizes, that may be used in the welding helmet assembly of FIGS. 6-7, in accordance with various aspects of the present invention.
Figure 8B:
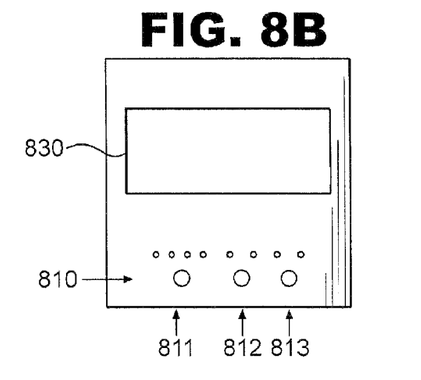
Figure 8C:
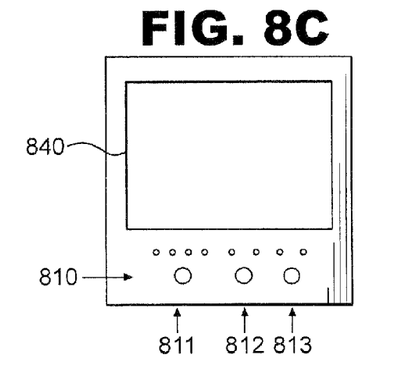

Whether the filter lens 630 is a fixed filter lens or an ADF shade cartridge, the filter lens 630 may include a filter window having one of at least three possible sizes where each next window size is larger in height than a previous window size (e.g., offering selections of "good", "better", and "best" window sizes). FIGS. 8A-8C illustrate three exemplary embodiments of auto darkening shade cartridges, having a common set of controls 810 and different window sizes 820, 830, and 840 which may be used in the welding helmet assembly 600 of FIGS. 6-7, in accordance with various aspects of the present invention.

In accordance with an embodiment of the present invention, the set of common controls 810 include a subset of shade controls 811, a subset of sensitivity controls 812, and a subset of delay/grind controls 813, which are well known in the art. Other combinations of controls are possible as well, in accordance with various alternative embodiments of the present invention. Again, the clear cover plate 660 may be slid upward far enough, from its normal position covering the first open window 611, such that the set of common controls 810 become accessible. In this way, a weldor can easily adjust the controls 810 without having to remove any elements from the welding helmet assembly 600. After the adjustments to the controls are made, the clear cover plate 660 is simply slid back downward into position over the window 611 to cover the controls 810.

In summary, welding helmet assemblies are disclosed having various adjustable and re-configurable features that allow the helmet assemblies to be very user-friendly. The spatter shield associated with any welding helmet assembly configuration disclosed herein is easily accessible and removable from a front portion of the helmet assemblies, without having to remove any filter lens for some embodiments. Also, the welding helmet assemblies disclosed herein each include a repositionable lever which allows a detent position of the helmet to be easily adjusted.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A re-configurable welding helmet assembly to be worn on a head of a weldor, said re-configurable welding helmet assembly comprising:
   a common shell having a first open window at a front portion of said common shell, wherein said common shell is adaptable to at least two different welding helmet configurations;
   an interior lens adapted to cover said first open window at an interior front portion of said common shell;
   an interior retaining mechanism adapted to retain said interior lens over said first open window;
   a front bezel having a second open window and being adapted to easily attach to and detach from an exterior front portion of said common shell such that said second open window aligns substantially with said first open window when said front bezel is attached to said common shell; and
   a spatter shield positioned externally to said common shell proximate said front portion of said common shell by, at least in part, said front bezel, such that said spatter shield is easily accessible from said external front portion of said common shell for replacement.

2. The re-configurable welding helmet assembly of claim 1 wherein said interior retaining mechanism comprises:
   an interior retaining frame adapted to help retain said interior lens at said interior front portion of said common shell over said first open window; and
   a de-latchable interior retaining clip adapted to secure said interior lens and said interior retaining frame in place at said interior front portion of said common shell over said first open window.

3. The re-configurable welding helmet assembly of claim 1 wherein said interior lens comprises one of a clear plastic lens, a fixed filter lens, and an automatic darkening filter shade cartridge.

4. The re-configurable welding helmet assembly of claim 1 wherein said spatter shield is held in position between said first open window of said common shell and said second open window of said front bezel when said front bezel is attached to said common shell, and wherein said spatter shield is easily accessible from said external front portion of said common shell for replacement by detaching said front bezel from said common shell and without having to remove any filter lens from said welding helmet assembly.

5. The re-configurable welding helmet assembly of claim 1 further comprising a flip bezel having a third open window and being adapted to attach to said front bezel such that said flip bezel is capable of flipping upward and downward, with respect to said front bezel, about a pivot axis at a top/front portion of said front bezel.

6. The re-configurable welding helmet assembly of claim 5 wherein said flip bezel is adapted to attach to said front bezel via a pivot pin and a lift spring attachably mounted between said flip bezel and said front bezel at said top/front portion of said front bezel.

7. The re-configurable welding helmet assembly of claim 5 wherein said spatter shield is positioned at an inside portion of said flip bezel to cover said third open window of said flip bezel.

8. The re-configurable welding helmet assembly of claim 7 further comprising a forward filter lens positioned directly behind said spatter shield away from said third open window.

9. The re-configurable welding helmet assembly of claim 8 wherein said forward filter lens comprises one of a fixed filter lens and an automatic darkening filter shade cartridge.

10. The re-configurable welding helmet assembly of claim 8 further comprising a clear cover plate positioned directly behind said forward filter lens away from said third open window.

11. The re-configurable welding helmet assembly of claim 10 further comprising a de-latchable forward retaining clip adapted to secure said clear cover plate, said forward filter lens, and said splatter shield in a sandwiched configuration at an inside portion of said flip bezel to cover said third open window of said flip bezel.

12. The re-configurable welding helmet assembly of claim 1 further comprising an adjustable ratchet headgear adjustably mounted within an interior of said common shell, via headgear mounting hardware, to fit a head of a weldor and to allow said common shell to tilt upward and downward with respect to said ratchet headgear.

13. The re-configurable welding helmet assembly of claim 12 further comprising a repositionable lever adjustably attached to one side of said ratchet headgear and adapted to adjust a detent position of said ratchet headgear with respect to said common shell, wherein said detent position determines a centering of said common shell with respect to said ratchet headgear by defining how far upward and how far downward said common shell can tilt with respect to a reference plane through said ratchet headgear.

14. The re-configurable welding helmet assembly of claim 13 wherein said repositionable lever may be locked into one of a plurality of detent positions via a tab on said adjustment lever that fits into one of a plurality of visible ridges on a side edge of said common shell, and wherein each visible ridge of said plurality of visible ridges corresponds to and identifies a different locked detent position of said plurality of detent positions.

15. The re-configurable welding helmet assembly of claim 12 wherein said headgear mounting hardware includes at least two washers, one mounted on each side of said common shell, adapted to provide friction between said common shell and said ratchet headgear to set a speed of tilt.

16. The re-configurable welding helmet assembly of claim 12 further comprising a sweatband removably attached to a front portion of said ratchet headgear such that said sweatband touches and spans a forehead of a weldor when said re-configurable welding helmet is properly fitted to and worn by said weldor.

17. A welding helmet assembly to be worn on a head of a weldor, said welding helmet assembly comprising:
a shell having a first open window at a front portion of said shell;
a bezel adapter having a second open window and being adapted to easily attach to and detach from an exterior front portion of said shell such that said second open window aligns substantially with said first open window when said bezel adapter is attached to said shell;
a filter lens adapted to fit securely between said first open window of said shell and said second open window of said bezel adapter when said bezel adapter is attached to said shell;
a bezel having a third open window and being adapted to easily attach to and detach from said exterior front portion of said shell over said bezel adapter such that said third open window aligns substantially with said second open window and said first open window when said bezel adapter and said bezel are attached to said shell;
a spatter shield adapted to fit securely between said second open window of said bezel adapter and said third open window of said bezel when said bezel adapter and said bezel are attached to said shell such that said spatter shield is easily accessible from said exterior front portion of said shell for replacement; and
a clear cover plate adapted to slide upward into an interior front portion of said shell to cover said first open window behind said filter lens.

18. The welding helmet assembly of claim 17 further comprising an adjustable cheater plate adapted to slide upward into said interior front portion of said shell behind said clear cover plate such that said cheater plate is adjustable, independent of said clear cover plate, to an eye level of a weldor using said welding helmet assembly.

19. The welding helmet assembly of claim 18 wherein said clear cover plate may be slid further upward to expose a set of common controls on a lower portion of said filter lens, whether or not said adjustable cheater plate is installed.

20. The welding helmet assembly of claim 18 wherein said clear cover plate may be removed from said shell by sliding said clear cover plate downward, whether or not said adjustable cheater plate is installed.

21. The welding helmet assembly of claim 17 wherein said clear cover plate is slidably held in position over said first window by a plurality of tabs on said shell surrounding said first window.

22. The welding helmet assembly of claim 18 wherein said adjustable cheater plate is slidably held in position by a plurality of tabs on said shell surrounding said first window.

23. The welding helmet assembly of claim 17 wherein said filter lens comprises a fixed filter lens.

24. The welding helmet assembly of claim 23 wherein said fixed filter lens includes a filter window having one of at least three possible sizes, each next window size being larger in height than a previous window size.

25. The welding helmet assembly of claim 17 wherein said filter lens comprises an automatic darkening filter shade cartridge.

26. The welding helmet assembly of claim 25 wherein said automatic darkening filter shade cartridge includes an ADF window having one of at least three possible sizes, each next window size being larger in height than a previous window size.

27. The welding helmet assembly of claim 26 wherein said automatic darkening filter shade cartridge includes a set of common controls on a lower portion of said cartridge, independent of said window size.

28. The welding helmet assembly of claim 27 wherein said set of common controls includes at least one of a subset of shade controls, a subset of sensitivity controls, and a subset of delay/grind controls.

29. A welding helmet assembly to be worn on a head of a weldor, said welding helmet assembly comprising:
a means for retaining at least one lens at a front portion of a shell of said welding helmet assembly to cover an open window of said shell;
a means for retaining a spatter shield at an external front portion of said shell such that said spatter shield is in substantial alignment with said open window;
a means for easily accessing said spatter shield for replacement at said external front portion of said shell without having to remove said at least one lens from said shell; and
a means to adjust a detent position, with respect to said shell, of an adjustable headgear mounted within said shell, wherein said detent position determines a centering of said shell with respect to said headgear by defining how far upward and how far downward said shell can tilt with respect to a reference plane through said headgear.

30. The welding helmet assembly of claim 29 wherein said at least one lens comprises at least one of a clear plastic lens, a fixed filter lens, and an automatic darkening filter shade cartridge.

31. The welding helmet assembly of claim 29 wherein said at least one lens is retained at an interior front portion of said shell covering said open window of said shell.

* * * * *